United States Patent
Imran

[11] Patent Number: 5,331,959
[45] Date of Patent: * Jul. 26, 1994

[54] LOW IMPEDANCE, LOW DUROMETER, DRY CONFORMING CONTACT MEMBER

[75] Inventor: Mir A. Imran, Palo Alto, Calif.

[73] Assignee: Physiometrix, Inc., Sunnyvale, Calif.

[*] Notice: The portion of the term of this patent subsequent to May 18, 2010 has been disclaimed.

[21] Appl. No.: 745,863

[22] Filed: Aug. 16, 1991

Related U.S. Application Data

[63] Continuation-in-part of Ser. No. 582,749, Sep. 14, 1990, Pat. No. 5,211,174.

[51] Int. Cl.$^5$ ............ A61B 5/04; A61N 1/05
[52] U.S. Cl. .................. 128/639; 128/641; 607/122; 252/500
[58] Field of Search ............... 128/639–641, 128/643, 644, 798, 802, 803; 607/149, 152, 153, 122

[56] References Cited

U.S. PATENT DOCUMENTS

| | | | |
|---|---|---|---|
| 4,237,886 | 12/1980 | Sakurada et al. | 128/798 |
| 4,248,247 | 2/1981 | Ware et al. | 128/798 |
| 4,515,162 | 5/1985 | Yamamoto et al. | 128/640 |
| 5,211,174 | 5/1983 | Imran | 128/639 |

FOREIGN PATENT DOCUMENTS

| | | | |
|---|---|---|---|
| 2521697 | 12/1975 | Fed. Rep. of Germany | 128/639 |
| 2045088 | 10/1980 | United Kingdom | 128/640 |
| 8402423 | 6/1984 | World Int. Prop. O. | 128/641 |

*Primary Examiner*—Lee S. Cohen
*Attorney, Agent, or Firm*—Flehr, Hohbach, Test, Albritton & Herbert

[57] ABSTRACT

Contact member comprised of a mass of nonconductive material having a low durometer and conductive elements dispersed in the mass of material in sufficient quantity to establish contact between the elements to provide a resistivity in the range of 10 to 100 ohm-cm.

10 Claims, 4 Drawing Sheets

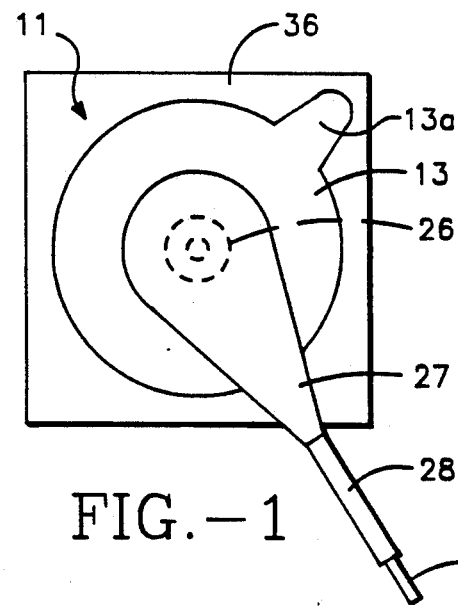
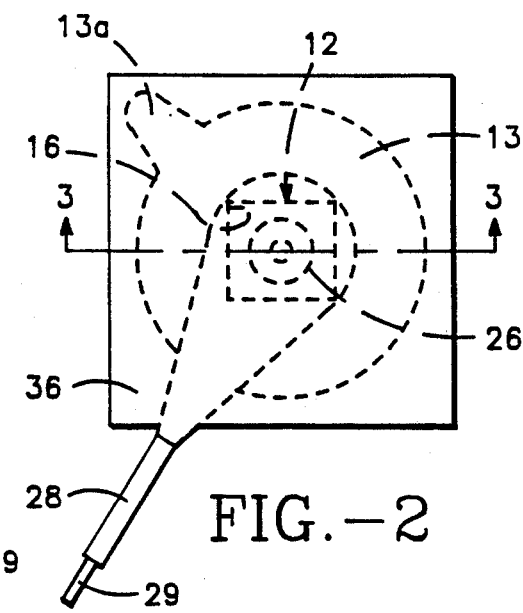
FIG.-1  FIG.-2
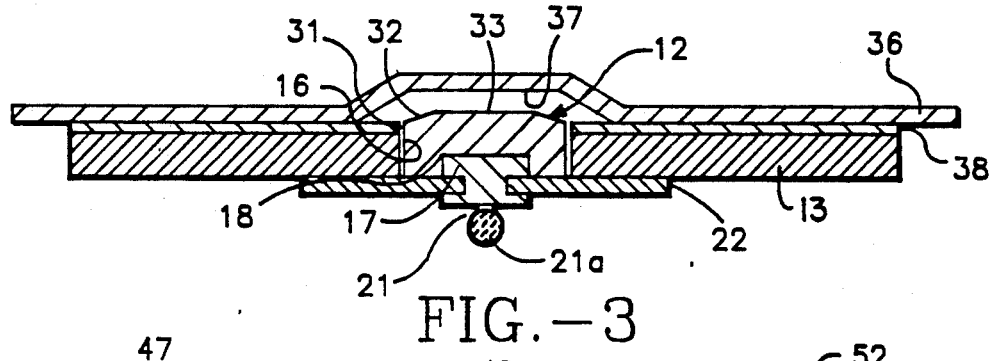
FIG.-3
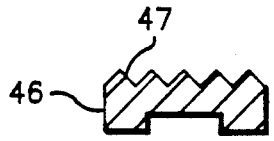  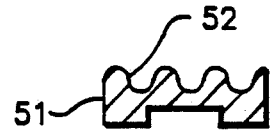
FIG.-4  FIG.-5  FIG.-6
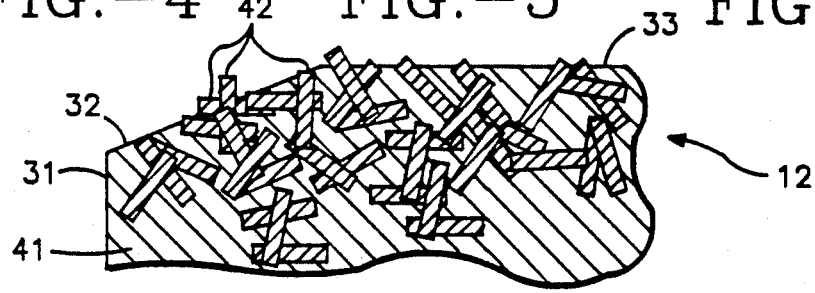
FIG.-7
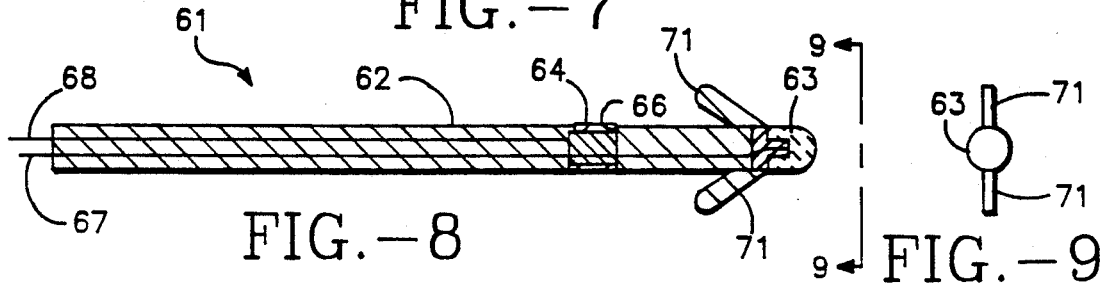 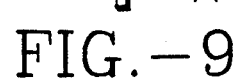
FIG.-8  FIG.-9

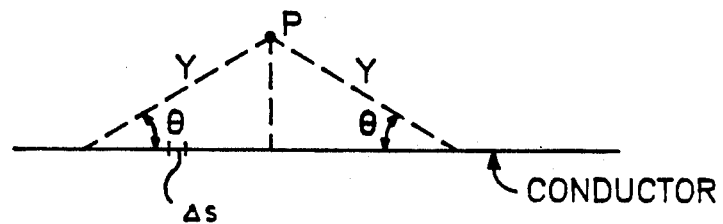
FIG.—14
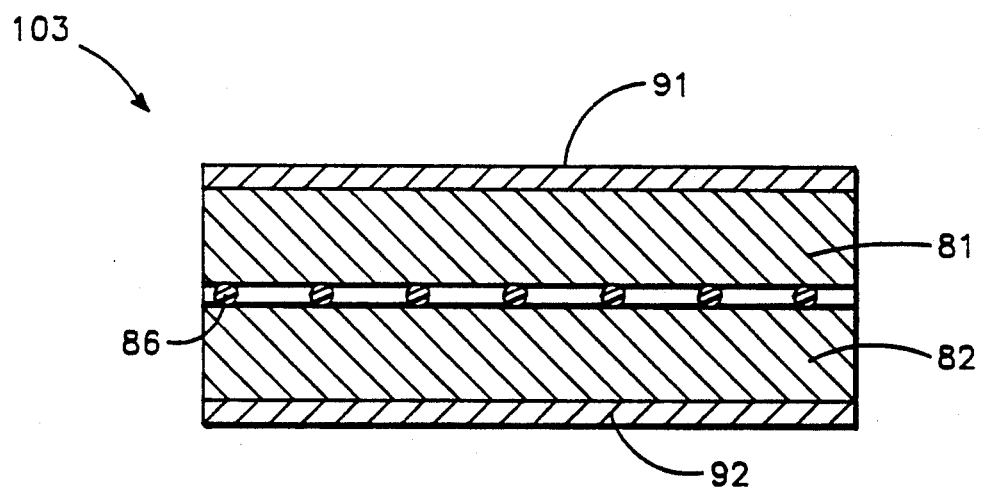
FIG.—11

5,331,959

LOW IMPEDANCE, LOW DUROMETER, DRY CONFORMING CONTACT MEMBER

CROSS REFERENCES TO RELATED APPLICATION

This application is a continuation-in-part of application Ser. No. 07/582,749 filed on Sep. 14, 1990, now U.S. Pat. No. 5,211,174.

FIELD OF THE INVENTION

This invention relates to a low impedance, low durometer, dry conforming contact member and method and device using the same.

BACKGROUND OF THE INVENTION

Electrodes of various types have heretofore been provided. For example, there are a number of electrodes which have been making ECG measurements. Typically, such electrodes have been of the disposable type and have been provided with a small foam pad which has been impregnated with a potassium chloride solution. This potassium chloride pad makes contact with the skin when it is in use. Before use, typically the device is covered with a plastic sheet to, in effect, enclose the same in an airtight vacuum to prevent it from drying out before use. To use the same, the plastic sheet is removed and the potassium chloride impregnated pad is brought into contact with the skin and held in contact therewith by a surrounding pad which is covered with an adhesive. Such electrodes have been found to have a number of disadvantages. They tend to dry out rather rapidly when placed into use. The impedance of the electrodes is fairly high in the range of 100-500,000 ohms, which increases as the pads dry out. In addition, it has been found that the potassium chloride solution has a tendency to irritate the skin and often gives patients a rash when worn more than several hours. This last undesirable characteristic is particularly noteworthy in the case of premature infants who have very sensitive skin. Presently available EEG electrodes have similar undesirable characteristics. There is therefore a need for a new and improved contact member which overcomes the above disadvantages.

OBJECTS OF THE INVENTION

In general, it is an object of the present invention to provide a contact member which has low impedance, has a low durometer and is dry (no free $H_2O$ additive), and a device and method for making the same.

Another object of the invention is to provide a contact member of the above character which can be utilized in EEG electrodes, ECG electrodes and pacemaker leads.

Another object of the invention is to provide a contact member of the above character which is not totally dependent upon ion flow across the interface between the electrode and the skin for conductivity.

Another object of the invention is to provide a contact member of the above character which is formable into a maintainable desired shape.

Another object of the invention is to provide a contact member of the above character which is moldable.

Another object of the invention is to provide a contact member which can be formed from a putty-like material.

Another object of the invention is to provide a contact member of the above character which can be provided in various predetermined stickinesses.

Another object of the invention is to provide a contact member of the above character which is very passive chemically and will not react with the skin.

Another object of the invention is to provide a contact member of the above character which can be worn for long periods of time by the patient without causing irritation or skin rashes.

Another object of the invention is to provide a contact member of the above character which is relatively inexpensive and which can be manufactured economically.

Additional objects and features of the invention will appear from the following description in which the preferred embodiments are set forth in detail in conjunction with the accompanying drawings.

BRIEF DESCRIPTION OF THE DRAWINGS

FIG. 1 is a top plan view of an electrode incorporating a contact member of the present invention.

FIG. 2 is a bottom plan view of the contact member shown in FIG. 1.

FIG. 3 is a cross-sectional view taken along the line 3—3 of FIG. 2.

FIGS. 4, 5 and 6 are cross-sectional views of alternative embodiments of contact members incorporating the present invention.

FIG. 7 is a greatly enlarged microscopic view of a portion of the contact member incorporating the present invention.

FIG. 8 is a partial side elevational view in cross section of a pacemaker lead incorporating contact members of the present invention.

FIG. 9 is an end elevational view looking along the line 9—9 of FIG. 8.

FIG. 11 is a cross-sectional view taken along the line 11—11 of FIG. 10.

FIG. 14 is a diagrammatic illustration showing how to calculate the magnetic field intensity around a conductive current.

DESCRIPTION OF PREFERRED EMBODIMENTS

Figure 10:
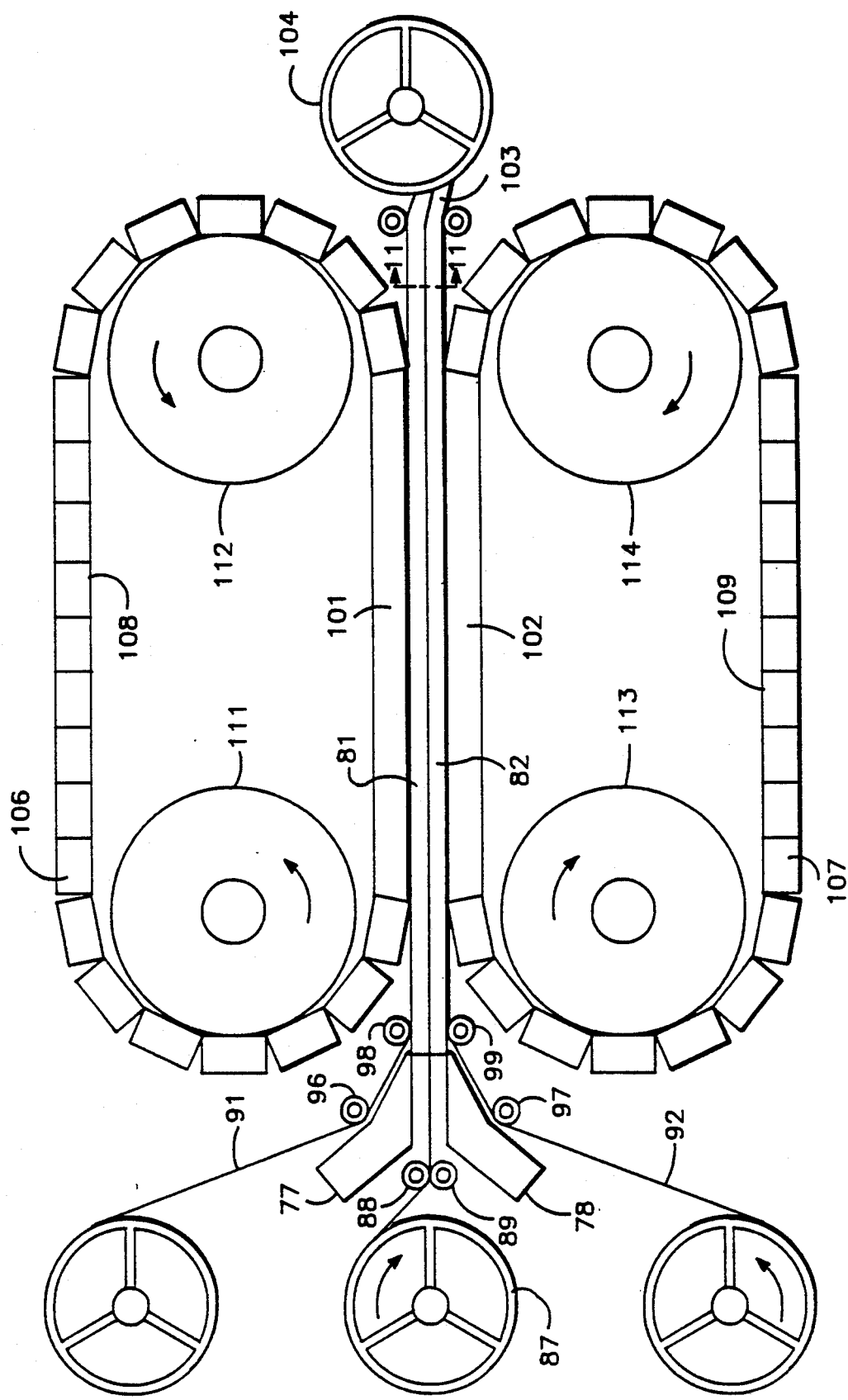
FIG. 10 is a schematic cross-sectional view of apparatus utilized in the manufacturing line for producing strip material from which contact members of the present invention can be made.

In general, it is an object of the present invention to provide a contact member comprising a mass of nonconductive material having a low durometer and conductive elements disposed in the mass of material in sufficient quantity to establish electrical contact between the elements so that the resistivity of the contact member ranges between 10-100 ohms-cm. It can be formed or molded so that it will retain its shape and will not be affected by gravity over substantial periods of time.

More specifically, in FIGS. 1, 2 and 3, an ECG electrode 11 is shown which incorporates therein a conductive silicone contact or member 12 incorporating the present invention. The electrode 11 is comprised of a flexible pad 13 formed of a suitable material such as a foam plastic. The pad 13 has a suitable configuration as for example circular with a dimension of approximately 1½ inches and a thickness of approximately 1/16th to ⅛th inch. The pad is provided with a tab portion 13a. The pad 13 is provided with a centrally disposed rectangular recess or opening 16. If desired, other geometries such as circular can be used.

A conventional conductive circular button 17 is disposed within the recess 16 and is formed of a suitable conducting material such as stainless steel which may be covered by a conductive coating 18 of a suitable type such as silver chloride coating. The button 17 is retained in the recess 16 in a suitable manner such as by securing the same to a conventional metal snap 21 which is secured to a flexible sheet 22 of relatively strong material such as a conventional plastic such as polyethylene or polysulfone by clamping the two parts comprised of the button 17 and the snap 21 onto the sheet 22. The outer margin of the sheet 22 extends over the recess 16 and over the inner margin of the pad 13 and is bonded to the pad 13 so as to support the button 17 within the recess 16. As shown in FIG. 3, the snap 21 is in the form of a male snap having a spherical protrusion 21a which is adapted to receive and engage a cooperating metal female snap 26 and frictionally engage the same and to make electrical contact therewith. The female snap 26 is carried by a termination 27 formed of a suitable material such as plastic which has a lead 28 bonded therein which carries a conductor 29 that is connected to the female snap 26.

The conductive silicone contact or member 12 is also disposed within the recess 16 and is in intimate contact with the button 17. The contact 12 can have any desired conformation. It is, as shown in FIGS. 2 and 3, is substantially rectangular in configuration of a size which is slightly less than the size of the recess 16. It is formed with a side wall 31 which fits within the recess 16. It is also provided with a tapered surface 32 which adjoins the sidewall 31 and also adjoins a generally planar contact surface 33.

Protective means is provided for protecting the conductive contact 12 from contamination prior to use and consists of a sheet 36 of a relatively flexible material such as plastic which is impervious to air. As shown, the sheet 36 can have any desired configuration as for example rectangular as shown in the drawings. This sheet is provided with a centrally disposed cup 37 which is adapted to receive the protruding surface 33 of the contact 12 when the sheet 36 is mounted on the pad 13. The pad 13 is provided with an adhesive 38 which is utilized for removably retaining the sheet 36 in engagement with the pad 13. The adhesive is also of a type which facilitates adhering the pad to the skin of a patient when the contact is in use. Adhesives of this type are well known to those skilled in the art and will not be described in detail.

The conductive silicone contact 12 is formed of a conductive silicone. The silicone when cured or polymerized is characterized in that it is dry with no free $H_2O$ additive and is very soft. It is nonconducting and has a tacky surface to the feel.

A silicone found to be particularly suitable for use in the present application is a two-component or two-part system, low viscosity liquid silicone gel manufactured by General Electric Company Silicone Products, Waterford, N.Y. 12188, identified as an RTV 6157 silicone gel. It cures at room temperature by use of a curing agent in a ratio of approximately 15:1 to 6:1. A softer gel having adhesive qualities is obtained by using less curing agent to optimize the stickiness with which the electrode is retained on the skin. It is free of solvents. It is transparent with a refractive index of 1.4. The cured gel permits a mechanical penetration of 8 mm with a Universal Penetrometer having a 69.5 gram aluminum shaft. As hereinafter described, when the gel and the catalyst are mixed together a silicone mass 41 is provided as shown in FIG. 7 in which conductive elements 42 are disposed. The conductive elements are formed of a material which is nonreactive to body fluids.

Figure 12:
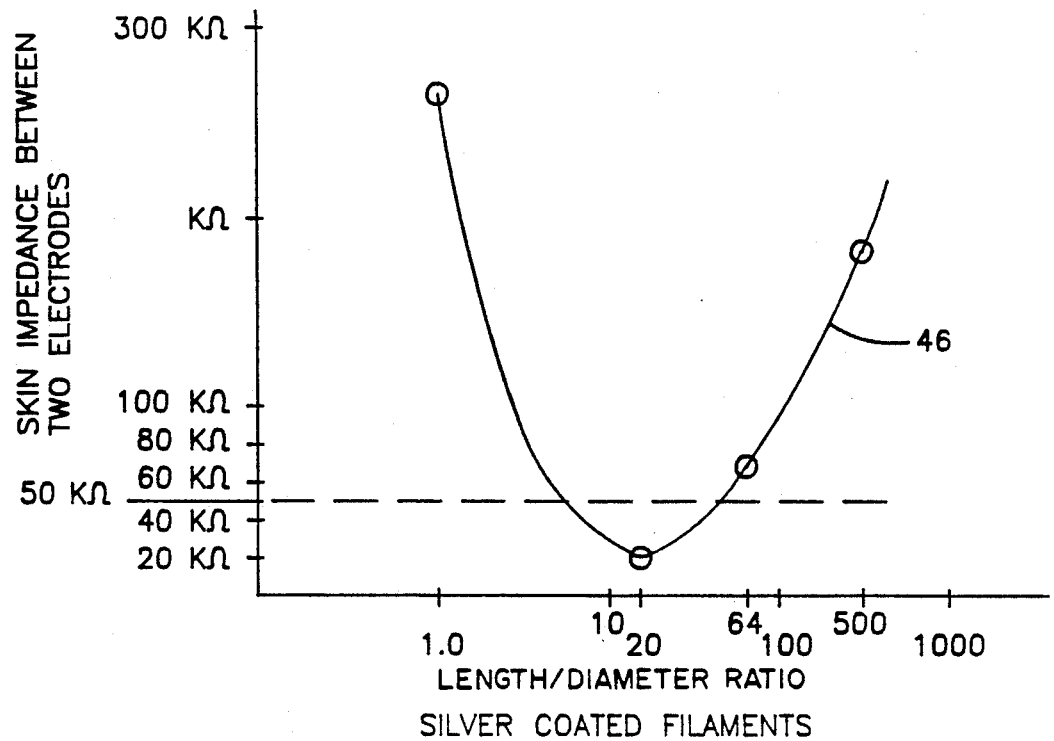
FIG. 12 is a graph showing the skin impedance between two electrodes of the present invention utilizing coated filaments of various length/diameter ratios.

One type of conductive element found to be particularly suitable for use in the present invention is a silver-coated particle manufactured by Potters Industries Inc., Waterview Corporate Center, 20 Waterview Boulevard, Parsippany, N.J. 07054, which can take the form of silver-coated fibers, silver-coated inorganic flakes, or silver-coated glass spheres. It has been found that the silver-coated cylindrical glass fibers provide the most desirable characteristics. The conductive elements 42 are in the form of silver-coated glass rods, filaments, fibers or cylinders. These silver-coated fibers combine the high conductivity of silver with the lightweight reinforcing properties of the fibers which protrude at least from the surface of the contact member in contact with the skin to act as conductive bridges across the contact member-skin interface. Particle size can range from 100 to 200 microns in length and 5 to 15 microns in diameter providing a length to diameter ratio of between 7 to 20. The particles have a silver coating which ranges from 2 to 6 percent silver by weight. Silver-coated glass fibers are utilized because they provide better conductivity because the fibers tend to contact each other more readily than would silver-coated glass spheres. For example, these can have a diameter of 5 to 20 microns and a length of 20 to 100 microns. The silver-coated glass flakes also provide a good conductivity, but not as good a conductivity as the silver-coated fibers. Silver-coated spheres have been found to be relatively non-functional in use in the contact member. This is shown in the graph of FIG. 12 which on the X axis shows the skin impedance between two electrodes of the present invention in a logarithmic scale in kilohms versus a Y axis also in a logarithmic scale of the length/diameter ratio of silver-coated elements or filaments of the present invention. Utilizing these parameters, a curve of 46 is established. From this curve, it is seen that when $L/D=1$ which is a sphere, the skin impedance is very high as for example approaching 300 kilohms, supporting the statement that silver-coated spheres are relatively non-functional in use in the contact member of the present invention. It also can be seen that to achieve a skin impedance of less than approximately 50 kilohms, it is desired to have an L/D ratio ranging from approximately 6 to 50. The graph in FIG. 12 also shows that rods or filaments of a certain length are best suited for use in the contact members of the present invention. Such rods or filaments actually protrude into the pores of he skin and thereby make good contact with the skin to reduce skin impedance.

By way of example, a silver-coated boro-silicate glass high-temperature ceramic can have a silver thickness ranging from 100 to 250 Å to provide a powder of 0.070 ohm-cm. Thicker coatings, as for example a silver-coating constituting 6 percent by weight providing a 520 Å silver thickness with a conductivity of 0.006 ohm-cm.

The silver-coated glass fibers can constitute a suitable percentage by weight of the composition which forms the pad 12, as for example 60 to 85 percent by weight of the total composition or mass with the silicone comprising the balance.

The silicone gel and the catalyst are in liquid form. They are poured into a suitable container and are stirred while the silver-coated glass fibers are mixed into the silicone to provide a thick paste-like consistency. The mixture is then dispensed through a syringe-like device into a suitable mold (not shown) having the conformation that is desired for the silicone contact 12. It is cured at a suitable temperature, as for example room temperature or at a suitable elevated temperature of 60° to 75° C. for a period of time ranging from 45 minutes to 1½ hours, and preferably at 65° C. for approximately 1 hour. After the composition has cured, it can be removed from the mold to provide the conductive silicone contact 12 which typically has a resistivity of 10–15 ohm-cm. The silicone composition or mass 41 which is formed with the silver-coated glass rods 42 within has a resistivity ranging typically from 10–15 ohm-cm. The pad has a consistency somewhat like Jello and has a slightly tacky or sticky surface when felt by the human hand. It typically is harder with the silver particles therein than the gel by itself. It still has a relatively low durometer value ranging from 20 to 50 on the scale of 0 to 100 of a PTC Model 302 SL Hardness Tester made by Pacific Transducer Corporation of 2301 Federal Avenue, Los Angeles, Calif. 90064. The PTC scale making these durometer measurements used a spring-loaded cylindrical probe having a circular contact surface of one square centimeter and using 100 to 120 grams of force. The scale of 20 to 50 translates into a penetration of the contact member by the probe of 4 to 2½ millimeters respectively. By utilizing a slightly higher proportion of catalyst it is possible to obtain a slightly stiffer contact pad having a higher durometer value.

As shown in FIG. 7, the conductive rods 42 extend through all of the outer surfaces of the silicone contact including 31, 32 and 33 to make good electrical contact with the skin of the patient and the coating 18 of the button 17. Because of the thousands of conductive rods 42 extending through the surfaces of the contact member 12, excellent electrical contacts are made between the contact member 12 and any surface it engages.

In certain applications for electrodes where additional tackiness or stickiness is desired, a putty-like mass can be formed by adding less catalyst and curing at a higher temperature, as for example about 300° F. for a period of about an hour.

The desired resistivity can be relatively carefully controlled by measuring the resistivity of the mixture during the time that the silver-coated glass rods or fibers are being introduced into the mixture. As soon as the desired conductivity is reached, no further silver-coated fibers are added. It has been found that the moldable mass which is produced for the contact member 12, after curing, is very stable over a long period of time, as for example years. It also has a very sticky or tacky surface which is a very important attribute for use in making an electrode to contact the skin, as for example the skin of a human. The low durometer of the contact member is also desirable because it permits the contact member to conform to the shape of the skin contour and thereby permits long-term use with patient comfort.

It has been found that the mixture can be kept indefinitely before curing by refrigerating the same at a suitable temperature, as for example at −25° to −45° C. When it is desired to utilize the same it can be brought out of the refrigerator and mixed again immediately prior to pouring into a mold to be sure that the silver-coated fibers have not settled out. As soon as the mold is subjected to a curing temperature, the mixture begins to cure. The mass is also particularly desirable for use as a contact member because in addition to being very stable it does not dry out or become brittle with time because it has no $H_2O$ additive. Thus it has a non-drying characteristic.

Although silver-coated rods or flakes have been disclosed as being the most preferable material known at the present time, it is possible to use other materials which are good conductors, as for example pure silver, gold and the like. However, using the pure materials without there being a carrier is unduly expensive. Therefore, it is most desirable to provide rods or filaments of the type hereinbefore described which are coated to provide the desired conductivity. In addition to silver and gold, other conductive metals, as for example nickel or copper, can be used. In addition, conductive materials such as graphite rods also can be utilized, even though there will be some sacrifice in conductivity. Conductivity as low as 100–200 ohm-cm can be achieved without skin preparation, which is within an acceptable range. Graphite, however, has a disadvantage in that graphite at the surface will have a tendency to rub off and leave a mark on the skin of the patient which may be undesirable to the patient. However graphite itself is inert and will not react to body fluids.

Although the electrode 11 has been discussed primarily for making ECG measurements, other skin type measurements can be made such as EMG (electromyogram for muscle potential measurement), EEG (electroencephalogram for making brain wave measurements), and EOG (for measuring eye motion over the eyebrows). The electrodes can also be used for electrical stimulation as in TENS or in defibrillation.

It has been found that the electrodes of the present invention are particularly useful in making EEG measurements because of the good conductivity which can be achieved without skin preparation.

In order to permit the skin to breathe beneath an electrode the contact surface 33 can be roughened. Thus, as shown in FIG. 4, a contact member 46 is provided which has sawtooth ridges 44 extending transversely thereof. In FIG. 5, a contact member 48 is provided which has U-shaped parallel recesses 49 extending transversely thereof. In FIG. 6, a contact member 51 is provided which has arcuate recesses 52 extending transversely thereof. These ridges and grooves permit air to circulate over the skin, permitting the skin to breathe.

The silicone contact or contact member 12 has the following specifications when tested against American National Standard pre-gelled disposable ECG and EEG electrodes having an electrolyte.

| Parameter | AAMI Requirement | Applicant's Silicone Contact |
|---|---|---|
| 1. Shelf Life | Use Before Date must be specified (typically 3 mos.) | >>one year |
| 2. AC Impedance | <2K Ω, for fresh | <5 Ω |

-continued

| Parameter | AAMI Requirement | Applicant's Silicone Contact |
|---|---|---|
| | electrodes | |
| 3. DC Offset Voltage | <100 mV after 1 minute | 0.00 V |
| 4. Offset Instability Internal Noise | <150 μV P—P in the Pass Band 0.15 Hz to 100 Hz | 0.00 V |
| 5. Defib. Recovery | <100 mV, 5 Sec. after Pulse | 0.00 V |
| 6. Bias Current Tolerance | <100 mV after 8 hours at 200 nA constant current | <1.0 μV |

The zero volts for DC offset, internal noise and defibrillation recovery arise because no electrolyte is present in the silicone contact of the present invention. The low impedance and the lack of an electrolyte reduces to a negligible value the voltage across the electrodes when subjected to a bias current.

It should be appreciated that the conductive silicone contact 12 described in the present invention can be utilized in other applications. One other medical application would be for a pacemaker lead 61 as shown in FIG. 8. Such a lead 61 is comprised of a flexible elongate element 62 formed of a plastic. A conductive tip 63 formed of the conductive silicone material shown in FIG. 8 is bonded to a conductor 67 carried by the member 67. A conductive band 64 also formed of the conductive silicone material of the present invention is seated within an annular recess 66 in the elongate element 62 and is bonded to a lead 68. Because of the characteristics of the silicone material, as for example the tackiness and the low durometer, the conductive tip 63 and the conductive band 64 make an excellent contact with the heart muscle to have it fibrose onto the lead 61. In order to facilitate anchoring of the conductive tip 63, the pacemaker lead 61 can be provided with fishhook-like elements 71 made of the same material as the flexible element 62.

Although the foregoing embodiments shown in FIGS. 1 through 9 have been described as utilizing a two-component, low viscosity, liquid silicone gel for the mass of nonconductive material which is particularly suitable for use in making moldable contact members, it has been found that other materials can be utilized in providing this nonconductive mass for use as a formable material rather than a moldable material. One such material is polybutene manufactured by Amoco Chemical Company, 200 East Randolph Drive, Chicago, Ill. 60601. This polybutene is a viscous, non-drying liquid. It is an isobutylene butene copolymer which is comprised predominantly of high molecular weight mono-olefins with minor isoparaffin content. The polybutene is colorless and resistant to oxidation by light and heat. It will not leave a residue when volatized or thermally decomposed. It has an important characteristic that in accordance with the present invention its tackiness or stickiness increases with increased molecular weight. It also has the characteristic of having less tackiness or stickiness when an additive such as mineral oil is added to the polybutene. One Amoco polybutene selected is identified as H-1900, which has the following characteristics:

| Viscosity, Saybolt Universal ASTM D2161, | |
|---|---|
| at 38° C. (100° F.), SUS | 788,000 |
| at 99° C. (210° F.), SUS | 19,700 |
| Molecular weight, number average vapor phase osmometry, M$_2$ | 2300 |
| Viscosity index ASTM D2270 | 122 |
| Evaporation loss ASTM D972, 10 hr at 99° C. (210° F.), wt % | 0.1 |

Although the H-1900 has very desirable characteristics, it should be appreciated that other polybutenes, as for example H-1500 which is supplied by Amoco, which for the Saybolt Universal Viscosity had values of 672,000 and 14,900 for the 38° C. and 99° C. characteristics. Thus it is believed that Saybolt Universal Viscosities in excess of 500,000 at 38° C. and 12,500 at 99° C. should be satisfactory. The viscosity of the H-1900 at room temperature is such that it will only pour very slowly from a container.

The polybutene is a polymer which does not contain any solvent. It can be used in food contact surfaces.

The polybutene hereinbefore described can be utilized as the nonconductive mass for making formable contacts of the type hereinbefore described. For example, the silver coated glass fibers hereinbefore described can be mixed in the same proportions hereinbefore described with the polybutene in an appropriate mixer, as for example a food mixer. In addition, in certain applications it may be desirable a water-absorbing type polymer to the mixture to make it possible for the contact made therefrom to absorb moisture, as for example perspiration from the skin of a human body. It is desirable that the water-absorbing type of polymer be one which absorbs moisture at room temperature, in other words at a temperature which is near that of the human body. One such water-absorbing polymer suitable for use in the present invention is Acrylamide (Electrophoresis Grade) which is in the form of white crystals. It has an absorbance of 50 g per 500 ml of distilled water, which indicates that it is very water absorbent. It becomes conductive in a 35% water solution to provide a conductivity of 2.5 μmhos maximum. The Acrylamide in the white powder form is mixed into the mixture during the time that the silver-coated glass fibers are introduced into the polybutene. The Acrylamide is supplied by Kodak. It should be appreciated that the same water absorbing polymer can be used for the same purpose in the moldable silicone based materials hereinbefore described.

The mixture hereinbefore described can be comprised of the following components by weight:

| polybutene | 32 grams |
|---|---|
| silver-coated fibers | 68 grams |
| acrylamide | 5 grams |

In the mixture above it should be appreciated that the silver-coated fibers can vary from 67 to 75 grams, and that the Acrylamide can vary from 3 to 10 grams, with the 68 grams of silver-coated fibers and the 5 grams of Acrylamide being the preferred amounts.

The mixture, after it has been made, can be formed into electrodes in the desired shape. The minimum desired conductivity can be obtained by utilizing 67 grams of the silver-coated fibers. Greater conductivity can be achieved by adding more of the silver-coated fibers.

The polybutene polymer has been found to be very sticky. It can be provided in a putty which can be readily formed into the desired shape. It will retain its shape over time when it is formed in relatively thin layers less than 0.050". Such a material particularly lends itself to screen printing. For example an electrode made from it having a diameter of approximately 0.3 inch, when adhered to a person's skin, is capable of supporting about 20–25 grams of weight, as for example the weight of a wire and the connector connected to the electrode when the electrode is in use. The polybutene hereinbefore described has the desired amount of tackiness so that it can support such a weight. This makes it particularly desirable for use for EEG and EMG and EOG electrodes.

The two-part, silicone-based mass hereinbefore described is formed from a two-part system in which a curing agent is utilized. In addition, it is a product which must be molded and then heated to a certain temperature to cause polymerization to take place. The polybutene, on the other hand, is a single-part system in which the quality of polymer itself is adequate for the present applications. It is merely necessary to add silver-coated fibers and the moisture absorbing Acrylamide to achieve the desired mass. There is no $H_2O$ additive. However, it is not a moldable material because it is rather in the form of a relatively fluid putty which maintains its consistency throughout its life. For example, it has no $H_2O$ content to evaporate. The tackiness or stickiness can be altered slightly by increasing or decreasing the amount of silver-coated fibers provided in the mass and by adding mineral oil. If it is desired to utilize the formable polybutene material in thicknesses greater than 0.050" in formed shapes over long times, it should be mechanically constrained from flow-type movement.

The apparatus needed for a manufacturing line to produce a mass of material which can be utilized for the production of electrodes in accordance with the present invention is shown in FIG. 10. The apparatus 76 which can be utilized for a manufacturing line for producing the silicone-based conductive material consists of first and second ejectors 77 and 78 which receive the premixed silicone-based material comprised of the silicone formed from a two-part system in which the silver-coated fibers have been introduced. A water-absorbing polymer such the Acrylamide hereinbefore described also can be utilized in connection with the silicone-based material. The ejectors 77 and 78 are supplied with the premixed material to supply two layers 81 and 82 (see FIG. 11) of the premixed material to a thickness of approximately 0.05" and a width of 6 inches. It should be appreciated that, in connection with the two ejectors 77 and 78, various options are available. For example, the Acrylamide material can be placed in only one of the layers, as for example the layer which is to face the skin of the patient. Alternatively, the mixture supplied to the ejectors 77 and 78 can be varied so that one of the layers, as for example 82, has a tackiness which is greater than the tackiness of the layer 81. Also the mixtures to the ejectors 77 and 78 can be varied by placing moldable silicone-based materials or formable polybutene in both ejectors or by a moldable material in one ejector and a formable material in the other ejector.

In order to increase the strength and reliability of the product produced by the manufacturing line in the form of the apparatus 76, a flexible sheet 86 formed of a suitable material such as Nylon mesh having a thickness ranging from 2 to 3 mils is introduced between the two ejectors 77 and 78 so that it passes between the layers 81 and 82. The Nylon mesh or fabric 86 (see FIG. 11) is supplied from a supply reel 87 through a pair of guiding rollers 88 and 89. The release liners 91 and 92 are applied over the exposed surfaces of the layers 81 and 82, and typically can be formed of a Mylar film having a thickness of 2 to 3 mils. The release liners 91 and 92 are supplied from supply reels 93 and 94 over guide rollers 96 and 97, and thereafter under guide rollers 98 and 99.

The layers 81 and 82, with the flexible fabric sheet therebetween and with the release liners 91 and 92, move through ovens 101 and 102 a suitable length of time to cure the silicone-based sheets 81 and 82 traveling therethrough. The ovens can be heated to a suitable temperature, as for example 300° F. and can have a length which is determined by the speed of travel of the layers 81 and 82 through the ovens. The composite sheet 103 which is formed from the layers 81 and 82, the fabric sheet 86 and the release liners 91 and 92 is taken up by a take-up reel 104. During the curing process, the layers 81 and 32 can be entrapped in molds 106 and 107, which are mounted upon endless belts 108 and 109. The endless belt 108 travels over drums 111 and 112 which rotate in a counterclockwise direction so that the lower run of the endless belt 108 travels in a direction towards the take-up reel 104. Similarly, the belt 109 is mounted upon rotating drums 113 and 114, which are rotated in a counterclockwise direction so that the upper run of the belt 109 also travels in a direction towards the take-up reel 104. Thus, it can be seen that the molds 106 and 107 serve to contain the siliconebased material during the time they are being cured or polymerized.

After reel 104 has been filled, the reel can be taken to other manufacturing locations where the composite sheet material 103 provided thereon can be utilized for manufacturing electrodes of the type hereinbefore described.

In conjunction with the foregoing, Mylar has been selected for the release liners 91 and 92 because it can withstand the relatively high heat within the ovens 101 and 102. The Mylar has a relatively high melting temperature and it is relatively nonreactive. The Nylon mesh can have a suitable mesh size, as for example $0.1 \times 0.1$ inch to $0.1 \times 0.05$ inch.

The width of the composite sheet can range from various sizes, as for example 0.5 inch to 0.75 inch wide tape, and alternatively can range to a width, as for example, as wide as 2 to 4 inches.

It should be appreciated that a similar type of apparatus can be utilized for manufacturing materials for electrodes of the present invention utilizing the polybutene hereinbefore described. Thus, for the two layers 81 and 82, two polybutene layers can be utilized, one stickier or tackier than the other. However, the ovens 101 and/or 102 could be eliminated when curing is not required.

It should be appreciated that other materials can be utilized in connection with the present invention for providing the nonconductive mass utilized. Thus, for example, polymers curable under ultraviolet light can be utilized in place of the heat-curable polymers hereinbefore described. Preferable examples of such ultraviolet curing polymers are as follows: Nuvasil 17631, 17614, 17412 supplied by Locktite Corporation.

Figure 13:
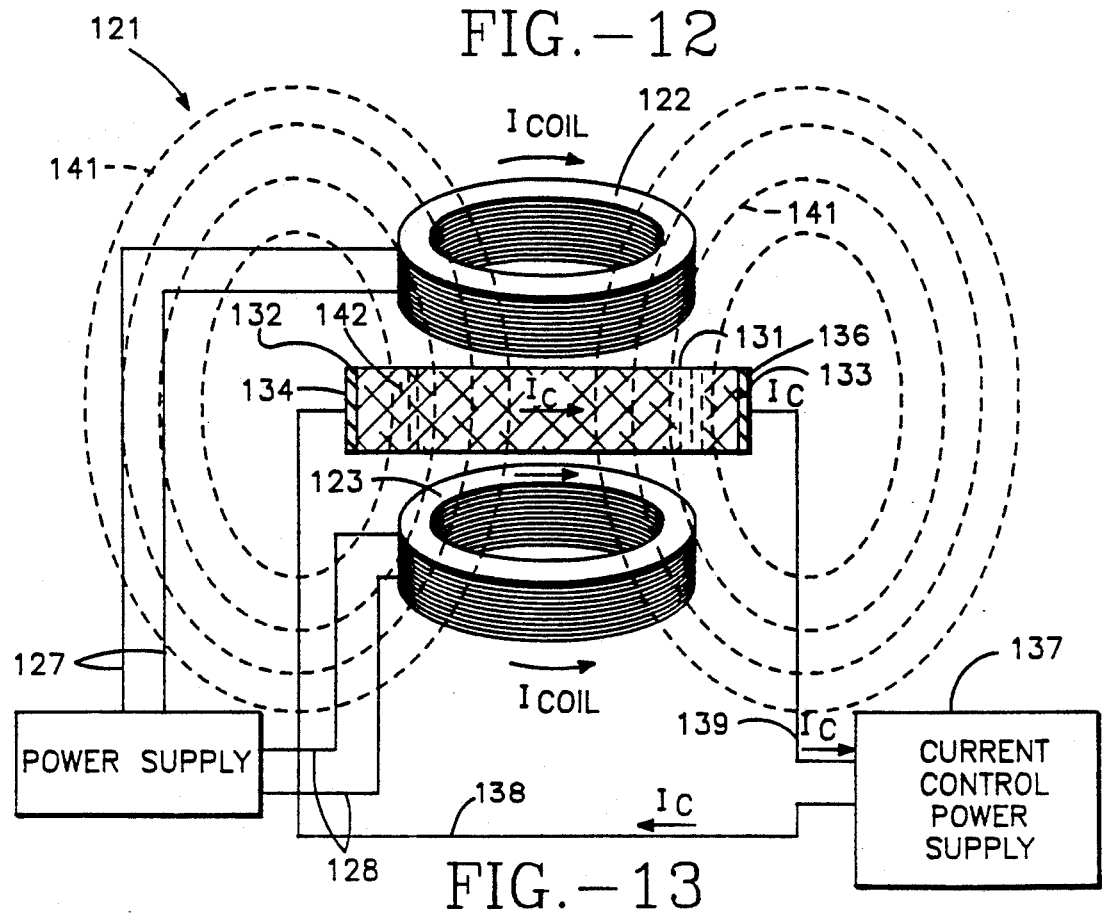
FIG. 13 is an elevational schematic view of a filament orientation system which can be used in connection with the present invention.

In applications where it is desired to achieve improved orientation of the metal-coated filaments or rods hereinbefore described, apparatus 121 of the type shown schematically in FIG. 13 can be utilized. Such an apparatus can consist of a pair of superposed doughnut-shaped coils 122 and 123 formed of insulated conducting wires (not shown) which are supplied with current from a power supply 126 by pairs of conductors 127 and 128. A mass 131 of the moldable material hereinbefore described is disposed between the coils 122 and 123 as shown in FIG. 13 having spaced apart surfaces 132 and 133 which are engaged by metallic contact members 134 and 136. The metallic contact members 134 and 136 are connected to a current control power supply 137 by conductors 138 and 139 to supply a controllable current identified as $I_c$ through the mass 131. The energization of the coils 122 and 123 creates lines of flux extending between the same certain of which extend in a direction which is generally perpendicular to the planes of the coils 122 and 123, and perpendicular to the line of travel of current from the metal contact 134 through the metal contact 136 coupled to the mass 131. This current flow through the mass 131 represented by $I_c$ establishes a magnetic force on the non-magnetic metal coated rods or filaments 142 disposed within the mass 131 to urge them to move in a direction within the mass to align themselves in the direction of the magnetic field, as for example to orient substantially all of the rods or filaments 142 in directions which are parallel to the magnetic lines of force created between the coils 122 and 123.

The field intensity which is needed to move the filaments or rods 142 into alignment with the magnetic flux lines is established by ascertaining the force generated on each particle due to the current $I_c$ and the magnetic field created by the coils 122 and 123 represented by the flux lines 141.

The force on a conductor carrying current in a magnetic field can be calculated by first calculating the magnetic field intensity at point P (see FIG. 14) created by the flow of current through the conductor by the equation:

$$H = \int \frac{I_c \sin\theta ds}{\gamma^2} \quad (1)$$

The above equation is a summation of the field $\Delta H$ at point P due to incrementally small segments of wire $\Delta s$.

When the above current carrying conductor is subjected to another magnetic field from a circular coil as shown in FIG. 13, a force is exerted on the current carrying conductor which is given by the equation:

$$F = H \times \frac{2\pi N I_c}{10\gamma} \text{ dynes} \quad (2)$$

where:
N is the number of turns;
$I_c$ is the coil current in amperes; and
$\gamma$ is the distance between the conductor and the coil.

By utilizing this interactive force, a substantial number of the filaments 142 can be oriented in the moldable polymer during the polymerization process so that the lengths or long dimensions of a large number of filaments 142 are approximately perpendicular to the surface of the electrode mass 131. The amount of force needed to orient the filaments is proportional to the initial viscosity of the polymer, the concentration of the filaments 142 in the polymer, and the length to diameter ratio of the filaments. The filaments 142 near the surface of the electrode will tend to orient themselves more readily than those below the surface.

This vertical orientation of a large number of filaments on the surface of the electrode is very desirable since it tends to reduce the impedance between the skin and the electrode.

In connection with the alignment of the rods or filaments as shown in FIG. 13, it is desirable to utilize a moldable material as for example a silicone-based material as hereinbefore described which can be polymerized or cured so that the rods or filaments 142 remain aligned in the desired directions after they have been subjected to the magnetic forces created in the apparatus shown in FIG. 13. The electric current $I_c$ utilized in the apparatus in FIG. 13 serves two purposes. For the first, it is to provide the current for passing through the rods or filaments 142 for causing their alignment as hereinbefore described, and secondly to provide the heat for polymerization or curing of the silicone-based material. If desired in order to speed up the process, additional heat can be supplied from external sources. It also is possible to utilize the apparatus shown in FIG. 13 for orienting the rods or filaments in ultraviolet curable materials by curing the same with ultraviolet light after the rods or filaments 142 have been oriented in the desired manner.

By orienting the rods or filaments within the mass of material, it is possible to achieve lower resistivities and improved conductivities and at the same time markedly improving the contact with the skin because of the protruding ends of the rods or filaments and thereby greatly reducing the impedance between the electrode and the skin.

It is apparent from the foregoing that there has been provided a low impedance, low durometer, dry conforming contact member and a method for making the same as well as devices for utilizing the same. The contact member is formed of a material which is dry and remains tacky over a long period of time which makes it an excellent material to contact the skin for making various types of skin measurements. It also conforms to the contours of the skin. The contact member also can be formed with a serrated surface permitting the skin to breathe. The contact member because of its sponginess can be worn for long periods of time as for example weeks without irritation to the skin. The wearer can bathe and take showers without removing the electrode or electrodes.

The contact member may include a moisture-absorbing polymer to absorb moisture from the skin of the patient. The contact member also can be provided with a reinforcing material to increase the structural strength of the contact member. The contact member can be formed in layers with the reinforcing material being disposed between the layers. Also, the layers can be formed of materials having different characteristics, as for example the surface of one layer can be more tacky than the surface of the other layer.

The contact members can be made in both moldable or formable (putty) forms. The low impedance at the skin interface is achieved by having ends of the metal-coated filaments or rods protrude from the contact member to mechanically contact the skin. In order to further improve this reduced impedance, the conductive elements in the form of the rods or filaments can be oriented in an electromagnetic field prior to curing and then cured to retain them in the desired positions. Different degrees of adhesiveness or stickiness or tackiness are achieved by changing the amount of catalyst added to the silicone-based materials. The polybutene formable material has a molecular weight of approximately 25000 when the desired viscousness is achieved and is still readily manufacturable into electrodes. The moldable material can be cured by ultraviolet light as well as by heat. By using laminations on both sides of a mesh material, two release strengths can be provided in the two layers as well as different thicknesses of the layers which makes it possible to customize the material so that the residue left on the skin and subsequent clean up is minimized. Also the two layers can be formable or moldable or alternatively both can be of the type. A smooth surface texture can be achieved on the moldable materials which is desirable for many applications, as for example defibrillator pads and Bovie pads. Such smooth surfaces can be achieved by eliminating air bubbles in the material during formulation and curing.

The contact member is constructed in such a manner so that it can be readily manufactured by mass production techniques utilizing molding and forming techniques.

What is claimed is:

1. A contact member comprised of a non-drying mass of nonconductive material having a low durometer and conductive elements dispersed in the mass of material in sufficient quantity to establish contact between the elements to provide a resistivity of less than 100 ohm-cm, said conductive elements having a length ranging from 100 to 200 microns and a diameter ranging from 5 to 20 microns and comprising more than 30% by weight of the contact member.

2. A contact member as in claim 1 wherein said mass of nonconductive material is a silicone gel.

3. A contact member as in claim 2 wherein said silicone gel is formed from a two-part system which includes a curing agent.

4. A contact member as in claim 1 wherein said mass of nonconductive material is a polybutene.

5. A contact member as in claim 4 wherein said polybutene is an isobutylene copolymer.

6. A contact member as in claim 1 wherein said mass of nonconductive material is a one-part system polymer.

7. A contact member as in claim 6 wherein said polymer is H-1900.

8. A contact member comprised of a non-drying mass of nonconductive material having a low durometer and conductive elements dispersed in the mass of material in sufficient quantity to establish contact between the elements to provide a resistivity of less than 100 ohm-cm and a reinforcing material disposed within the mass to impart additional structural strength to the mass, said conductive elements having a length ranging from 100 to 200 microns and a diameter ranging from 5 to 20 microns and comprising more than 30% by weight of the contact member.

9. A contact member as in claim 8 wherein said reinforcing material is a flexible fabric disposed as a layer in the mass.

10. A contact member as in claim 9 wherein said flexible fabric is a Nylon mesh.

* * * * *